US011691797B2

(12) United States Patent
Clarke et al.

(10) Patent No.: US 11,691,797 B2
(45) Date of Patent: Jul. 4, 2023

(54) STERILIZABLE POUCHES FOR MEDICAL DEVICES

(71) Applicant: Medtronic Vascular, Inc., Santa Rosa, CA (US)

(72) Inventors: David Clarke, Ballybrit (IE); Kate Molan, County Clare (IE); Christopher Faherty, Galway (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 346 days.

(21) Appl. No.: 16/871,739

(22) Filed: May 11, 2020

(65) Prior Publication Data

US 2020/0361684 A1    Nov. 19, 2020

Related U.S. Application Data

(60) Provisional application No. 62/848,560, filed on May 15, 2019.

(51) Int. Cl.
| | |
|---|---|
| *B65D 75/30* | (2006.01) |
| *B65B 55/02* | (2006.01) |
| *B65B 5/04* | (2006.01) |
| *A61B 50/30* | (2016.01) |
| *A61L 2/26* | (2006.01) |

(Continued)

(52) U.S. Cl.
CPC .............. *B65D 75/30* (2013.01); *A61B 50/30* (2016.02); *A61L 2/206* (2013.01); *A61L 2/26* (2013.01); *B65B 5/045* (2013.01); *B65B 55/02* (2013.01); *A61B 2050/0066* (2016.02); *A61B 2050/316* (2016.02); *A61L 2202/181* (2013.01); *A61L 2202/24* (2013.01)

(58) Field of Classification Search
CPC .... B65D 75/30; A61B 50/30; A61B 2050/316
USPC ................................................ 206/439, 484
See application file for complete search history.

(56) References Cited

U.S. PATENT DOCUMENTS

| | | |
|---|---|---|
| 3,552,638 A | 1/1971 | Quackenbush |
| 3,991,881 A | 11/1976 | Augurt |

(Continued)

FOREIGN PATENT DOCUMENTS

| | | |
|---|---|---|
| DE | 1941545 A1 | 7/1970 |
| DE | 4229314 A1 | 3/1994 |

(Continued)

OTHER PUBLICATIONS

International Search Report dated Sep. 3, 2020 corresponding to International Application No. PCT/US2020/032730.

*Primary Examiner* — Steven A. Reynolds
(74) *Attorney, Agent, or Firm* — Medler Ferro Woodhouse & Mills PLLC

(57) ABSTRACT

A flexible, sterilizable pouch includes a first gas-impermeable web, a second gas-permeable web, and the third gas-impermeable web. The webs are arranged and sealed to form a cavity portion of the pouch and a header portion of the pouch. The header portion of the pouch is gas-permeable through the second gas-permeable web. The cavity portion of the pouch is configured to hold a medical device for sterilization and is configured to be sealed from the header portion after sterilization, thereby making the cavity portion gas-impermeable. The header is also configured to be removed from the pouch, leaving the cavity portion.

17 Claims, 11 Drawing Sheets

(51) Int. Cl.
*A61L 2/20* (2006.01)
*A61B 50/00* (2016.01)

(56) References Cited

U.S. PATENT DOCUMENTS

| | | | |
|---|---|---|---|
| 4,270,658 A | 6/1981 | Schuster | |
| 4,407,874 A | 10/1983 | Gehrke | |
| 4,465,188 A | 8/1984 | Soroka et al. | |
| 4,660,721 A | 4/1987 | Mykleby | |
| 5,263,587 A | 11/1993 | Elkin et al. | |
| 5,562,211 A * | 10/1996 | Simons | A61B 17/06133 |
| | | | 206/813 |
| 5,564,570 A | 10/1996 | Jaszai | |
| 5,647,480 A | 7/1997 | Insley et al. | |
| 5,653,090 A | 8/1997 | Weiss et al. | |
| 5,791,476 A | 8/1998 | Stekloff | |
| 5,947,287 A | 9/1999 | Weiss et al. | |
| 6,251,489 B1 | 6/2001 | Weiss et al. | |
| 7,000,770 B2 | 2/2006 | Clarke et al. | |
| 7,066,331 B2 | 6/2006 | Koyanagi et al. | |
| 7,631,760 B2 | 12/2009 | Guelzow et al. | |
| 7,762,044 B2 | 7/2010 | Clarke et al. | |
| 8,123,035 B2 | 2/2012 | Won | |
| 8,689,976 B2 * | 4/2014 | Wittrock | B65B 7/02 |
| | | | 206/459.1 |
| 2005/0067312 A1 * | 3/2005 | Gupta | A61L 2/206 |
| | | | 206/524.1 |
| 2005/0268573 A1 | 12/2005 | Yan | |
| 2009/0169134 A1 | 7/2009 | Hsu | |
| 2009/0188826 A1 * | 7/2009 | Porteous | B65D 5/4216 |
| | | | 206/459.5 |
| 2009/0200198 A1 * | 8/2009 | Guelzow | B65D 81/3261 |
| | | | 422/4 |
| 2011/0139650 A1 | 6/2011 | Dworak | |
| 2011/0192121 A1 | 8/2011 | Kannankeril et al. | |
| 2012/0205269 A1 * | 8/2012 | Ludvig | A61L 2/00 |
| | | | 206/363 |
| 2014/0133785 A1 | 5/2014 | Diviesti et al. | |
| 2014/0262894 A1 | 9/2014 | Jansen | |
| 2015/0314940 A1 | 11/2015 | Matta | |
| 2018/0085180 A1 * | 3/2018 | Hillas | A61L 2/206 |
| 2019/0016518 A1 | 1/2019 | Cheich | |

FOREIGN PATENT DOCUMENTS

| | | |
|---|---|---|
| EP | 0306207 A1 | 3/1989 |
| EP | 1520795 A1 | 4/2005 |
| EP | 2460506 A1 | 6/2012 |
| FR | 2348109 A1 | 11/1977 |
| GB | 1569479 | 6/1980 |
| WO | 1996039340 A1 | 12/1996 |
| WO | 2005073091 A2 | 8/2005 |

* cited by examiner

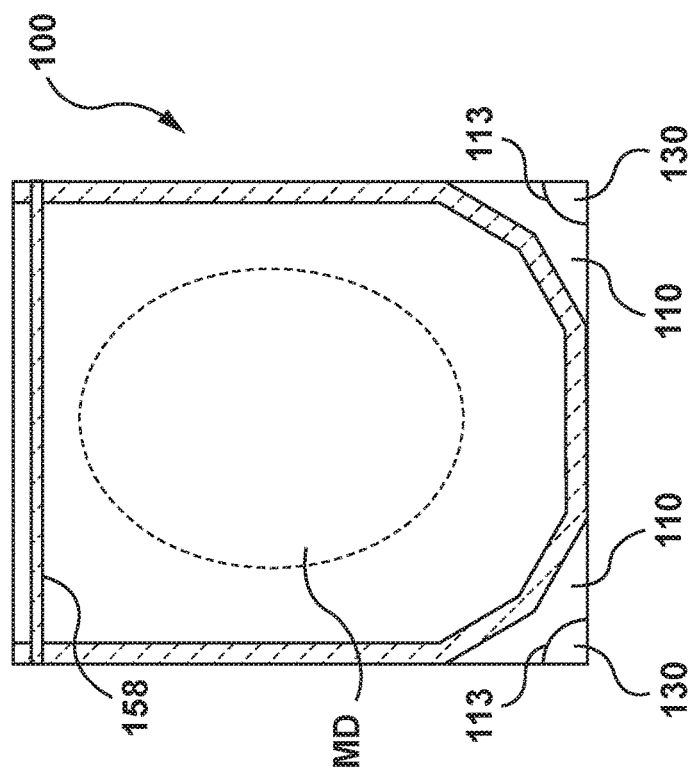
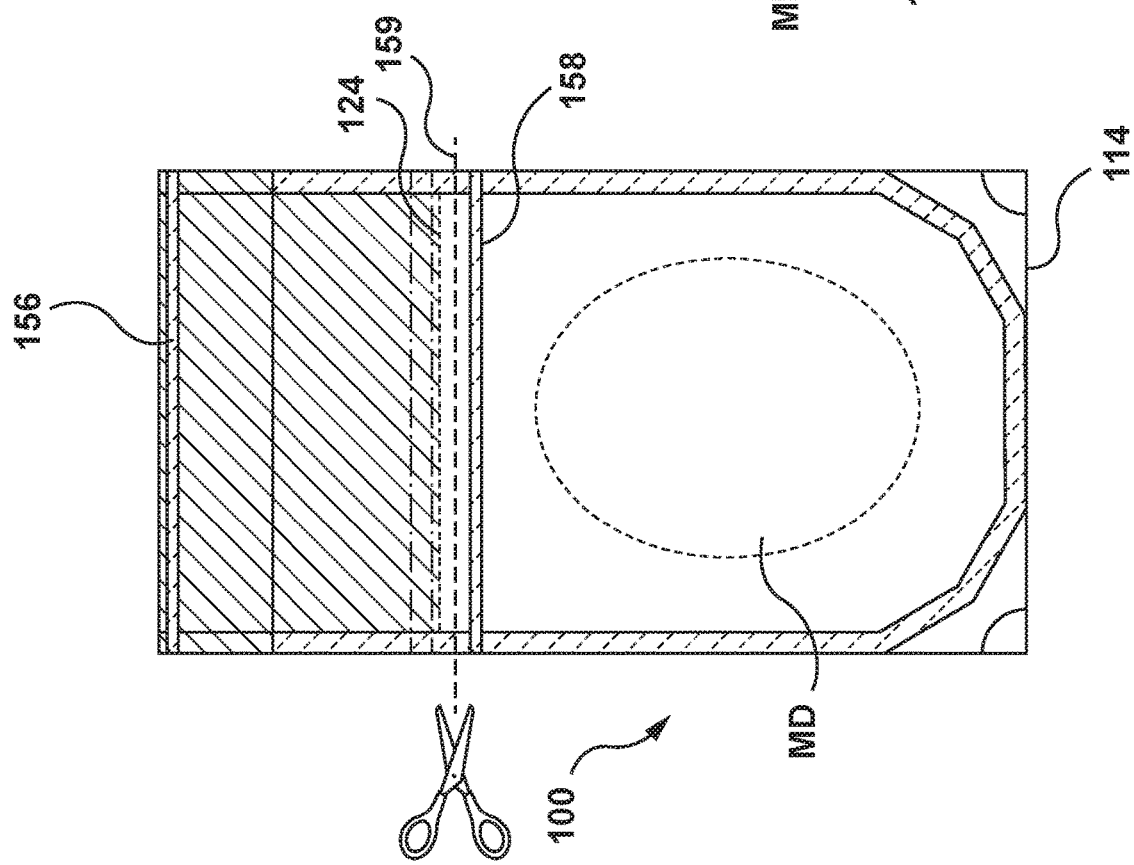
FIG. 6
FIG. 7

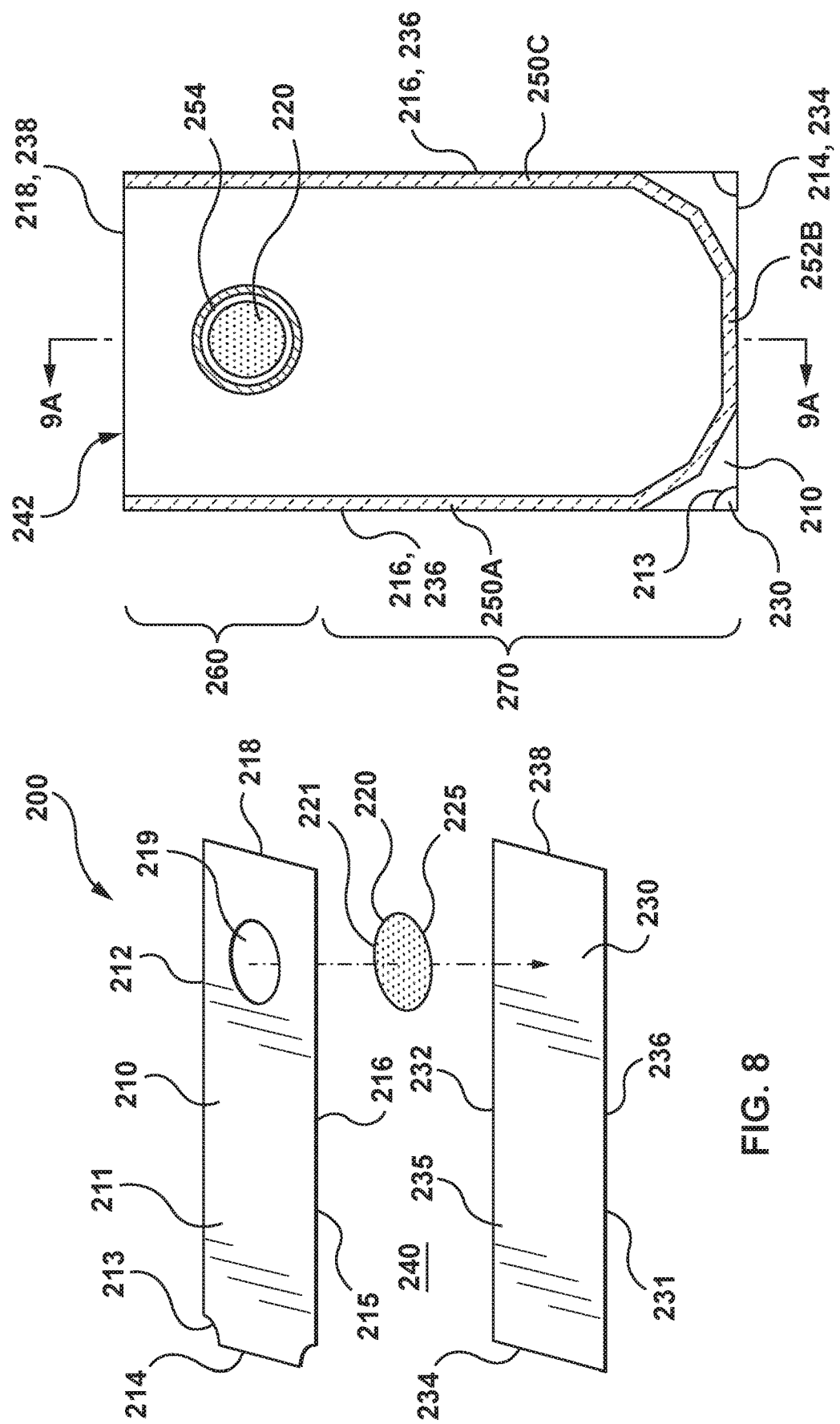

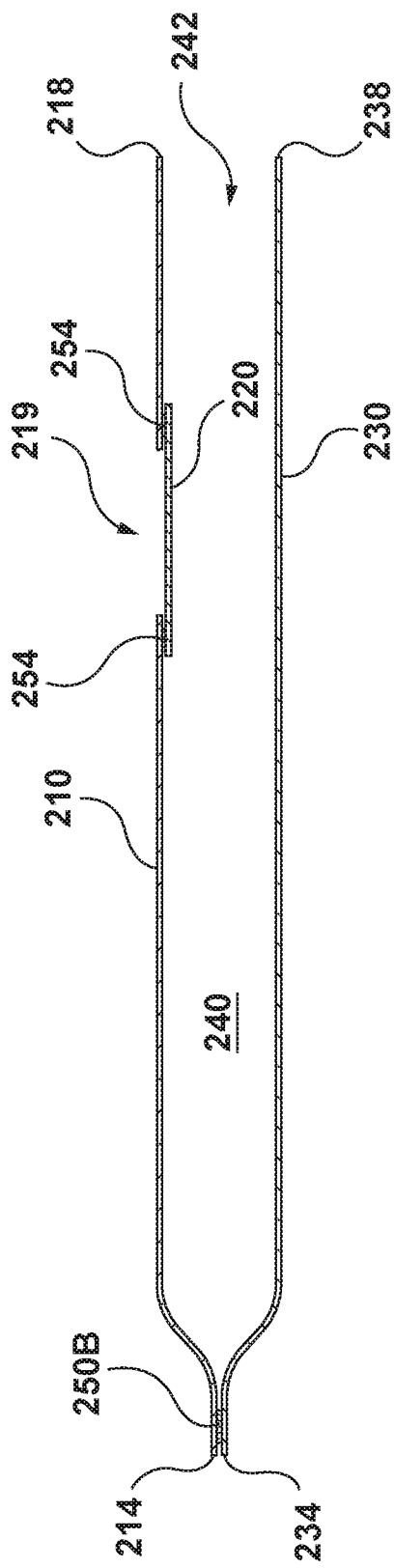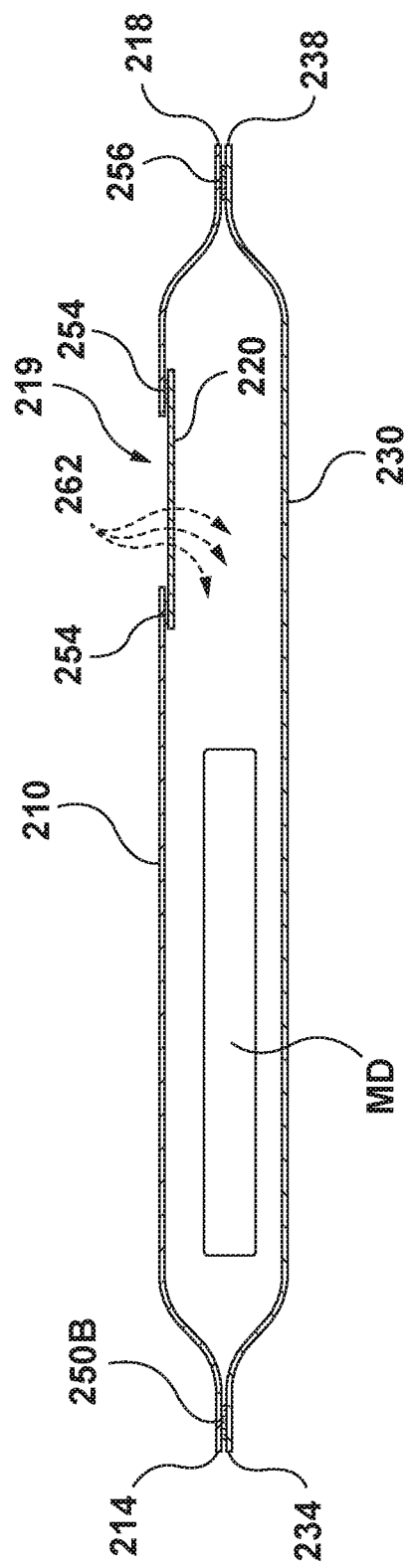

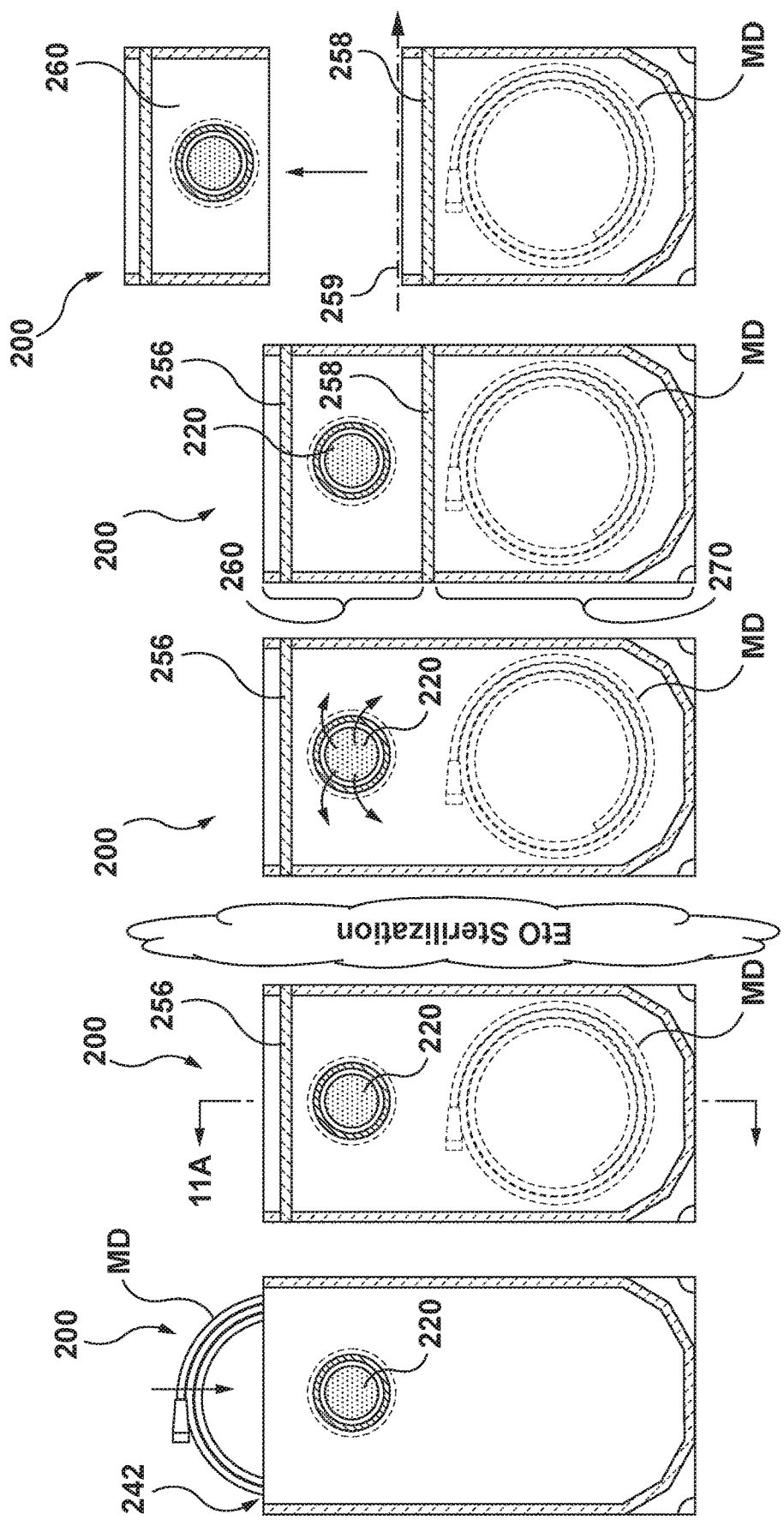

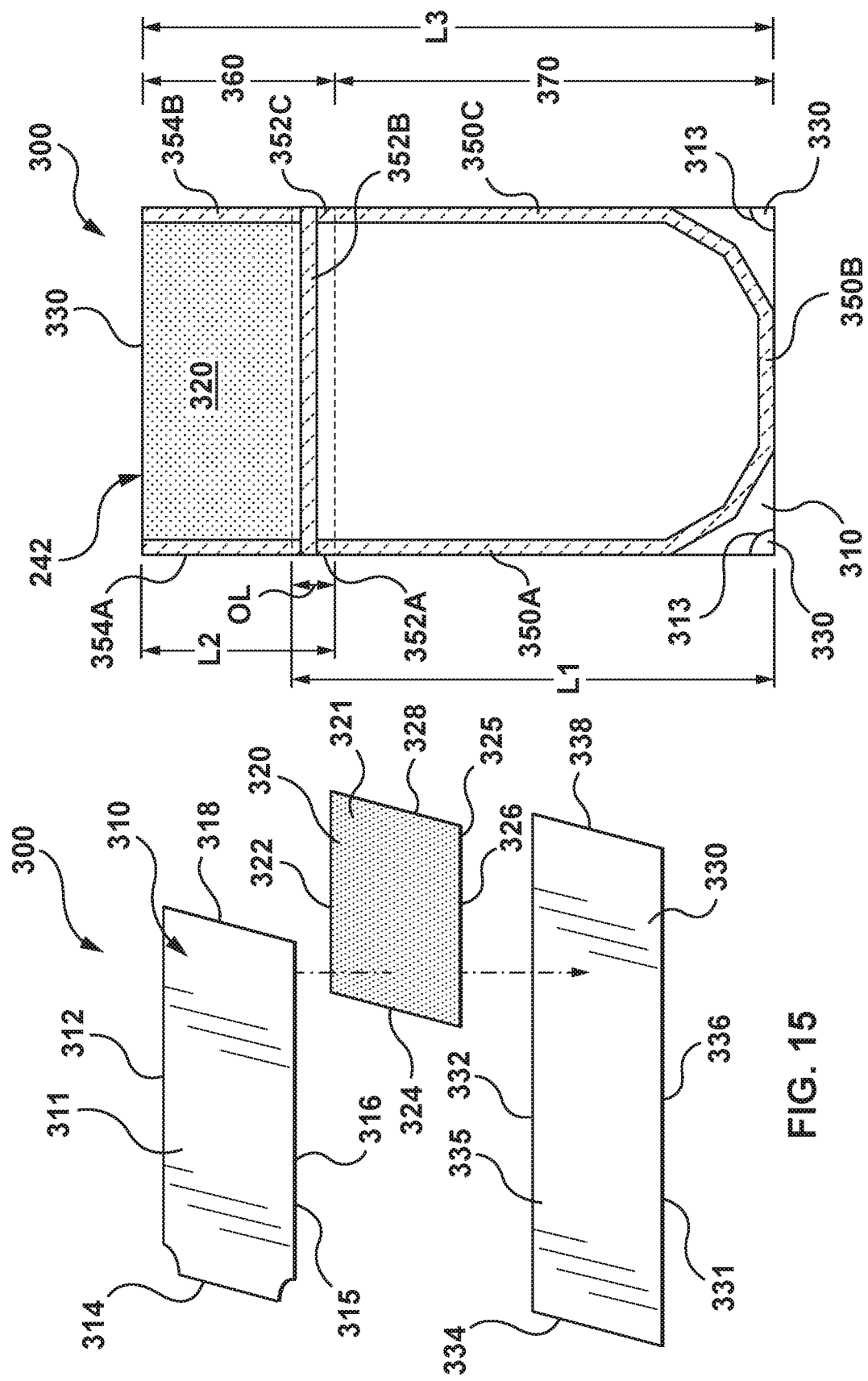

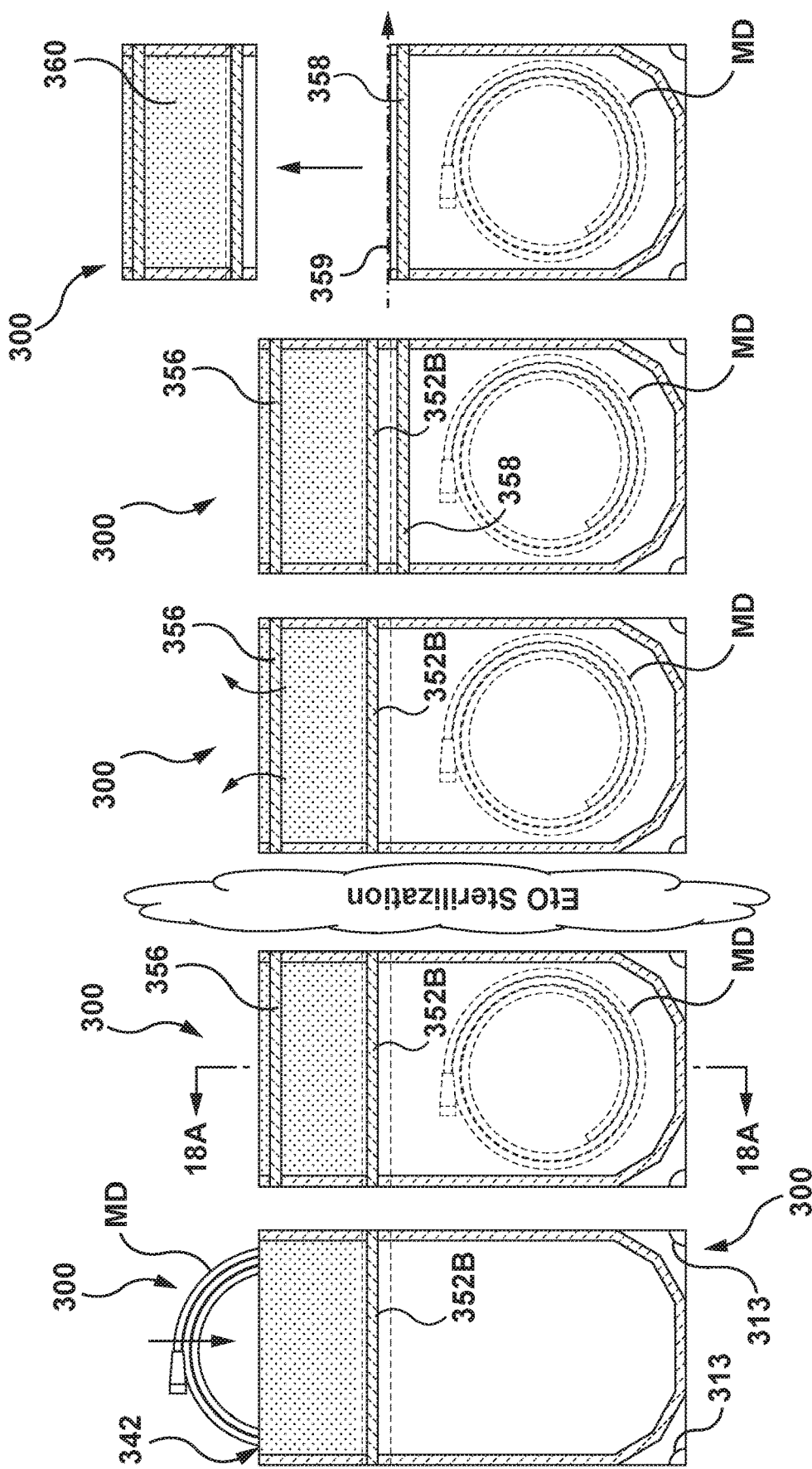

STERILIZABLE POUCHES FOR MEDICAL DEVICES

CROSS-REFERENCE TO RELATED APPLICATIONS

The present application claims the benefit of the filing date of U.S. provisional application No. 62/848,560, filed May 15, 2019, the contents of which are incorporated by reference herein in their entirety.

FIELD OF THE INVENTION

The present invention relates to sterilizable, flexible medical device pouches.

BACKGROUND OF THE INVENTION

Sterilizable, flexible pouches, hereafter referred to as pouches, for maintaining the sterility of objects, such as medical devices, for surgical applications have been utilized for many years. Such pouches typically utilize a bag fabricated from flexible, non-porous plastics such as polyethylene and/or gas-permeable materials such as a DuPont product called Tyvek®. Sterilization is accomplished after sealing the medical device within the pouch by exposing the sealed pouch to, for example, a sterilization gas such as ethylene oxide (EtO) or steam, or radiation such as an electron beam or gamma radiation.

When using ethylene oxide for sterilization, for example, the ethylene oxide must be able to reach the medical device within the pouch. Ethylene oxide cannot penetrate non-porous plastic such as polyethylene. Accordingly, a gas-permeable path from outside of a pouch to the medical device within the pouch is needed for certain sterilization methods (e.g. ethylene oxide). However, after sterilization, this gas-permeable path permits oxygen and other gasses to penetrate the pouch, which is not desirable. Therefore, oxygen absorbers and/or desiccants (moisture absorbers) are used with pouches, which adds cost and may not be entirely effective. In the alternative, or in addition to, other ways to make the pouch gas-impermeable are used, which may add cost or complexity to the sterilization process.

Accordingly, there is a need for a simple and effective pouch that is gas-permeable during sterilization and then may be made gas-impermeable after sterilization.

BRIEF SUMMARY OF THE INVENTION

Embodiments herein are directed to a flexible, sterilizable pouch including a first gas-impermeable web having a first length, a second gas-permeable web having a second length, and a third gas-impermeable web having a third length. The third length is longer than the first and second lengths such that with first end edges of the first and second webs aligned, a second end edge of the third web extends past a second end edge of the first web. A cavity is formed between the first and third webs. A header is defined from a first end edge of the second web overlapping with the second end edge of the first web and sealed to an inner surface of the first web to a second end edge of the second web aligned with the second end edge of the third web with the second web sealed to an inner surface of the third web.

In some embodiments, an opening is formed between the second end edge of the second web and the second end edge of the third web due to the respective second end edges of the second and third webs not being sealed to each other. The opening is configured to be sealed after a medical device is inserted therethrough and into the cavity, thereby forming a sealed pouch that is gas-permeable through the header. In some embodiments, the cavity of the pouch is configured to be made gas-impermeable by a seal between the first web and the third web formed after a sterilization process, wherein the seal is generally parallel to the first and second end edges of the first and third webs, and wherein the seal is disposed longitudinally between the first end edge of the second web and the first end edges of the first and third webs. In some embodiments, the header is configured to be removed after the seal between the first and third webs is formed.

Embodiments herein are also directed to a method of sterilizing a medical device and sealing the medical device within a pouch. The method includes inserting the medical device through an opening in the pouch. The pouch includes a first gas-impermeable web, a second gas-permeable web, and a third gas-impermeable web, wherein the first and third gas-impermeable webs are sealed to each other along corresponding first and second side edges and first end edges of the first and third webs, wherein a second end edge of the third web extends past a second end edge of the first web, wherein a first end edge of the second gas-permeable web is sealed to an inner surface of the first web adjacent the second end edge of the first web, wherein the second web is sealed to the third web along corresponding first and second side edges of the second and third webs, and wherein the opening is formed by corresponding second end edges of the second and third webs that are not attached to each other. The method further includes sealing the opening after inserting the medical device through the opening. The method further includes exposing the pouch to a sterilizing gas under conditions to sterilize the medical device, wherein the sterilizing gas reaches the medical device through the second gas-permeable web. The method further includes, after sterilizing the medical device, removing air from the cavity and forming a final seal between the first and third webs generally parallel to the first and second end edges of the first and third webs, wherein the final seal is located longitudinally between the first end edge of the second web and the first end edges of the first and third webs. In some embodiments, after forming the final seal, the method further includes removing a portion of the pouch between the final seal and the second edge edges of the second and third webs.

Embodiments herein are also directed to a flexible, sterilizable pouch including a first gas-impermeable web, the first web including a hole extending from an outer surface thereof through an inner surface thereof, a second gas-permeable web being sealed to the inner surface of the first web and covering the hole, a third gas-impermeable web sealed to the first web along corresponding first and second side edges and corresponding first end edges of the first and third webs, and an opening formed at corresponding second end edges of the first and third webs, wherein the opening is formed by the second edge edges of the first and third webs not being attached to each other. The hole is offset towards the second end edge of the first web such that a cavity portion of the pouch configured to hold a medical device is defined longitudinally between the first end edges of the first and third webs and the hole, and a header portion of the pouch is defined from a side of the hole closest to the first end edge of the first web to the second end edge of the first web.

In some embodiments, the opening is configured to be sealed after a medical device is inserted therethrough and into a cavity of the cavity portion, thereby forming a sealed pouch that is gas-permeable through the hole and the second web. In some embodiments, the pouch is configured to be made gas-impermeable by a seal between the first web and the third web formed after a sterilization process, wherein the seal is generally parallel to the first and second end edges of the first and third webs, and wherein the seal is disposed longitudinally between the side of the hole closest to the first end edge of the first web and the first end edges of the first and third webs. In some embodiments, the header portion of the pouch is configured to be removed after the seal between the first and third webs is formed.

Embodiments herein are also directed to a method of sterilizing a medical device and sealing the medical device within a pouch. The method includes inserting the medical device through an opening in the pouch, the pouch including a gas-impermeable first web including a hole extending from an outer surface thereof through an inner surface thereof, a second gas-permeable web sealed to the inner surface of the first web and covering the hole, and a third gas-impermeable web, the third web being sealed to the first web along corresponding first and second side edges and corresponding first end edges of the first and third webs, wherein the opening is formed by corresponding second end edges of the first and third webs that are not attached to each other. The method further includes sealing the opening after inserting the medical device through the opening. The method further includes exposing the pouch to a sterilizing gas under conditions to sterilize the medical device, wherein the sterilizing gas reaches the medical device through the hole and the second gas-permeable web. The method further includes, after sterilizing the medical device, removing air from the pouch and forming a final seal between the first and third webs generally parallel to the first and second end edges of the first and third webs, wherein the final seal is located longitudinally between the first end edge of the second web and a side of the opening closest to the first end edge of the first web. In some embodiments, the method further includes after forming the final seal, removing a portion of the pouch between the final seal and the second edge edges of the first and third webs.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 6 is a schematic plan view of another step in the method of sterilization and sealing of a medical device within the pouch of FIG. 1 in accordance with an embodiment hereof.

FIG. 7 is a schematic plan view of the pouch of FIG. 1 after the method of sterilization and sealing of a medical device within the pouch has been completed.

FIG. 8 is a schematic exploded view of a pouch in accordance with another embodiment hereof.

FIG. 9 is a schematic plan view of the pouch of FIG. 8.

FIG. 9A is a schematic sectional view taken along line 9A-9A of FIG. 9.

FIG. 10 is a schematic plan view of a step in a method of sterilization and sealing of a medical device within the pouch of FIG. 8 in accordance with an embodiment hereof.

FIG. 11 is a schematic plan view of another step in the method of sterilization and sealing of a medical device within the pouch of FIG. 8 in accordance with an embodiment hereof.

FIG. 11A is a schematic sectional view taken along line 11A-11A of FIG. 11.

FIG. 12 is a schematic plan view of another step in the method of sterilization and sealing of a medical device within the pouch of FIG. 8 in accordance with an embodiment hereof.

FIG. 13 a schematic plan view of another step in the method of sterilization and sealing of a medical device within the pouch of FIG. 8 in accordance with an embodiment hereof.

FIG. 14 a schematic plan view of another step in the method of sterilization and sealing of a medical device within the pouch of FIG. 8, and shows the pouch of FIG. 8 after the method of sterilization and sealing of a medical device within the pouch has been completed.

FIG. 15 is a schematic exploded view of a pouch in accordance with another embodiment hereof.

FIG. 16 is a schematic plan view of the pouch of FIG. 15.

FIG. 17 is a schematic plan view of a step in a method of sterilization and sealing of a medical device within the pouch of FIG. 15 in accordance with an embodiment hereof.

FIG. 18 is a schematic plan view of another step in the method of sterilization and sealing of a medical device within the pouch of FIG. 15 in accordance with an embodiment hereof.

FIG. 19 is a schematic plan view of another step in the method of sterilization and sealing of a medical device within the pouch of FIG. 15 in accordance with an embodiment hereof.

FIG. 20 a schematic plan view of another step in the method of sterilization and sealing of a medical device within the pouch of FIG. 15 in accordance with an embodiment hereof.

FIG. 21 a schematic plan view of another step in the method of sterilization and sealing of a medical device within the pouch of FIG. 15, and shows the pouch of FIG. 15 after the method of sterilization and sealing of a medical device within the pouch has been completed.

DETAILED DESCRIPTION OF THE INVENTION

Specific embodiments of the present invention are now described with reference to the figures, wherein like reference numbers indicate identical or functionally similar elements.

The following detailed description is merely exemplary in nature and is not intended to limit the invention or the application and uses of the invention. Although the description of embodiments hereof is in the context of pouches used for sterilization, storage and transportation of medical devices, pouches described herein can also be used in other applications and for other devices. Furthermore, there is no intention to be bound by any expressed or implied theory presented in the preceding technical field, background, brief summary or the following detailed description.

Embodiments of the present invention disclose a multi-layer, sterilizable, and flexible medical device pouch (hereafter referred to as a "pouch") also referred to as a bag, receptacle, or compartment.

Figure 1:
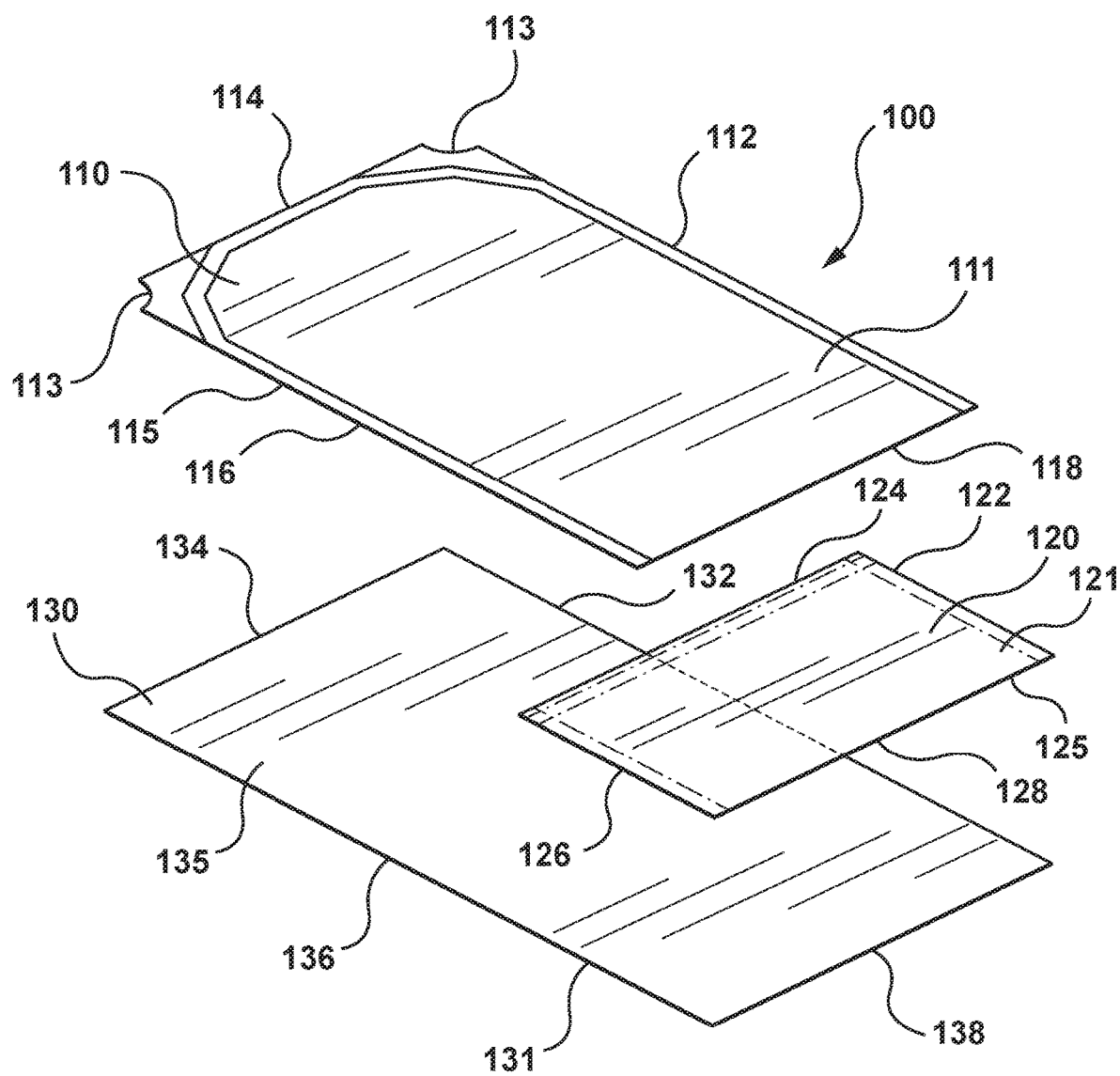
FIG. 1 is a schematic exploded view of a pouch in accordance with embodiments hereof.
Figure 2:
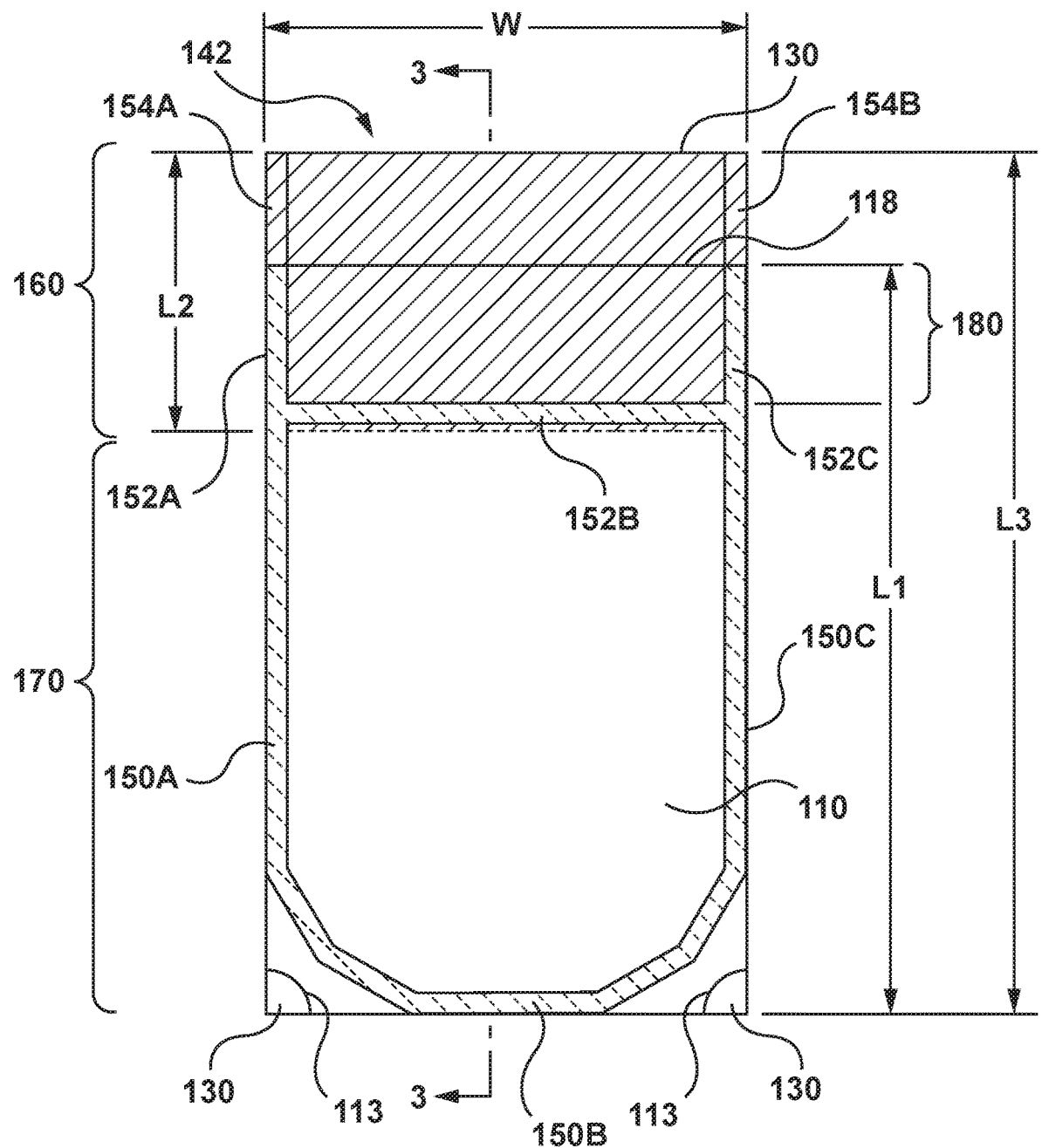
FIG. 2 is a schematic plan view of the pouch of FIG. 1.
Figure 3:
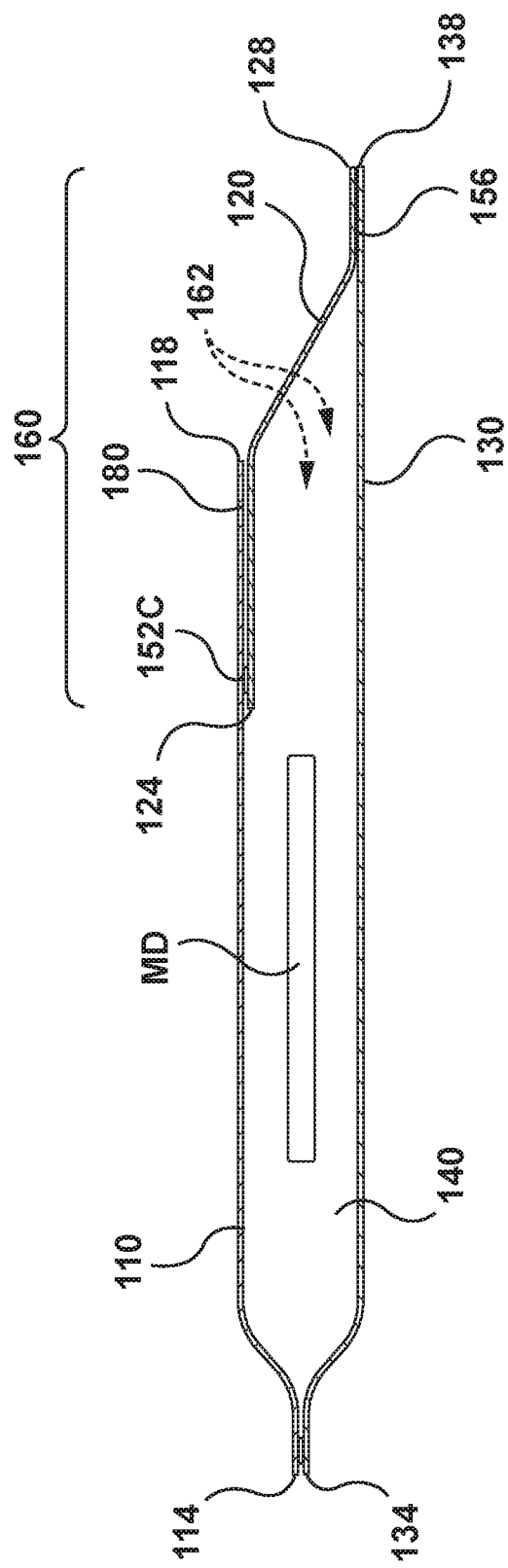
FIG. 3 is a schematic sectional view taken along line 3-3 of FIG. 2.

A pouch 100 in accordance with an embodiment hereof is shown in FIGS. 1-7. FIG. 1 shows an exploded view of the pouch 100. As can be seen in FIG. 1, the pouch 100 includes a first layer or web 110, a second layer or web 120, and a third layer or web 130, wherein the second web 120 is disposed partially between the first web 110 and the third web 130. In this specification, the first web 110 may also be referred to as a top layer or web, the second web 120 may be referred to as a middle layer or web, and third web 130 may be referred to as a bottom layer or web. However, it is recognized that labels regarding orientation, such as top and bottom, are not limiting in that the pouch 100 may be flipped such that the third web 130 is "on top". As used herein the term "layer" or "web" means a formed sheet that may be a laminate of several layers formed together. Thus, a laminate with several materials formed together as a single sheet is a single layer or web, not more than one layer, as would be understood by those skilled in the art. A cavity 140 for receiving a medical device MD is formed between the first web 110 and the third web 130, as shown in FIG. 3.

In the embodiment of FIGS. 1-7, the first web 110 is formed of a gas-impermeable film or foil material, such as, but not limited to aluminum, low-density polyethylene (LDPE), nylon, or polyester. The first web 110 provides an effective barrier against the migration of micro-organisms, including bacteria. In an example, and not by way of limitation, the first web 110 may be a material known as Polyester Foil Laminate RFR-085 available from Amcor. Similarly, the third web 130 is formed of a gas-impermeable film or foil material, such as, but not limited to aluminum, low-density polyethylene (LDPE), nylon, or polyester. The third web 130 may be formed of the same material and the first web 110, but it may be a different gas-impermeable material. For example, and not by way of limitation, in an embodiment, the third web 130 may be a material known as Plyester/Foil Core Peel LCP-545 available from Amcor. In the embodiment of FIGS. 1-3, the second web 120 is a gas-permeable material that is a barrier to microorganisms, but is permeable to gases including oxygen, carbon dioxide, and various sterilization gases such as, but not limited to ethylene oxide gas (EtO), steam sterilization methods, and other suitable sterilization methods. Suitable materials for the second web 120 may include medical grade paper and nonwoven sheet materials. Suitable nonwoven sheet materials include spun-bond nonwoven fabrics such as Typar® and Reemay® fabrics from Fiberweb Inc. Suitable materials also include spun-bonded polyolefin marketed by DuPont under the name Tyvek®. In an example, and not by way of limitation, the second web 120 may be a material known as 1059B Uncoated Tyvek available from DuPont. The example materials provided above are not limiting. However, in the embodiment of FIGS. 1-7, the first and third webs 110, 130 are gas-impermeable, and the second web 120 is gas-permeable, as those terms are understood by those skilled in the art.

The first web 110 includes first and second side edges 112, 116, first and second end edges 114, 118, an outer surface 111, and an inner surface 115. The first web 110 may also include cut-outs 113 where the first and second side edges 112, 116 meet the first end edge 114, as shown in FIGS. 1 and 2, for easy of peeling the first web 110 from the third web 130, as described in more detail below. Similarly, the second web 120 includes first and second side edges 122, 126, first and second end edges 124, 128, a first surface 121, and a second surface 125. Similarly, the third web 130 includes first and second side edges 132, 136, first and second end edges 134, 138, an inner surface 135, and an outer surface 131. Although cut-outs 113 are described with respect to the first web 110, cut-outs could instead be provided in the third web 130. Referring to FIG. 2, the first web 110 has a first length L1, the second web 120 has a second length L2, and the third web 130 has a third length L3. The third length L3 of the third web 130 is greater than the first length L1 of the first web 110, which is greater than the second length L2 of the second web 130. In a non-limiting example, the first length L1 may be approximately 13.5 inches, the second length L2 may be approximately 5 inches, and the third length L3 may be approximately 15.5 inches. In an embodiment, a width W of each of the first, second, and third webs 110, 120, 130 are equal. In a non-limiting example, the width W may be approximately 8.625 inches. The example dimensions are non-limiting and may be varied depending on the size of the pouch desired at least partially based on the size of the medical device MD to be contained in the cavity 140. Because the third web 130 is longer than the first web 110, with the first end edges 114, 134 of the first and third webs 110, 130 aligned, the second end edge 138 of the third web 130 extends past the second end edge 118 of the first web 110, as shown in FIGS. 2 and 3. As also shown in FIGS. 2 and 3, the length L2 of the second web 120 is such that with the second end edge 128 of the second web 120 aligned the second end edge 138 of the third web 130, the first end edge 124 of the second web 120 is disposed between the first and second end edges 114, 118 of the first web 110, thereby forming a header 160. In an embodiment, the first web 110 overlaps with second web 120 for approximately 3 inches between the second end edge 118 of the first web and the first end edge 124 of the second web 120.

Having described how the webs 110, 120, 130 are oriented relative to each other, the seals connecting the webs to each other will now be described with reference to FIG. 2. In the embodiment shown, the first web 110 is coupled to the third web 130 at seals 150A, 150B, and 150C. The seals 150A, 150B, and 150C form a generally U-shape and extend generally along first side edges 112, 132, first end edges 114, 134, and second side edges 116, 136 of the first and third webs 110, 130. As shown in FIG. 2, along the first and second side edges 112, 132, 116, 136, the seals 150A, 150C begin where the overlapping of the first web 110 and the second web 120 ends. The seals 150A, 150B, and 150C are preferably peelable seals (also known as "peel seals"), as known to those skilled in the art. Peelable seals 150A, 150B, 150C enable easy removal of the medical device MD from the pouch 100 when the medical device MD is ready to be used. Peelable seals 150A, 150B, 150C also ease the method of aseptic technique practiced when removing the medical device MD from the pouch 100.

Still referring to FIG. 2, the first web 110 is sealed the second web 120 at seals 152A, 152B, and 152C. The seal 152A is between the first web 110 and the second web 120 along respective first side edges 112, 122 where the first and second webs 110, 120 overlap. Similarly, the seal 152C is between the first web 110 and the second web 120 along respective second side edges 116, 126 where the first and second webs 110, 120 overlap. The seal 152B is between the first web 110 and the second web 120, extends generally parallel to the first end edge 122 of the second web 120, and extends from the seal 152A to the seal 152C. In the embodiment of FIGS. 1-7, due to the location of the seal 152B adjacent the first end edge 124 of the second web 120 and the amount of overlap between the first and second webs 110, 120, a pocket 180 is formed between the first web 110 and the second web 120. The pocket 180 is defined by the seals 152A, 152B, 152C, the inner surface 115 of the first web 110, the first surface 121 of the second web 120, and the second end edge 118 of the first web 110, which is not sealed to the second web 120. The pocket 180 permits standard flushing sealers that include flushing arms to open the pocket 180 with the flushing arms such that a nozzle of the flushing sealer can extend into the pocket 180 between the first web 110 and the second web 120 to flush the cavity 140. At the location of seals 152A, 152B, and 152C, the third web 130 is located adjacent the second web 120 (i.e., below the second web 120 in FIG. 2), but the third web 130 is not sealed to the second web 120 or the first web 110 at the locations of the seals 152A, 152B, and 152C. In an embodiment, the seals 152A, 152B, and 152C are weld seals, as that term is understood by those skilled in the art.

Still referring to FIG. 2, the second web 120 is coupled to the third web 130 at seals 154A and 154B. Seal 154A is between the second web 120 and the third web 130 along respective first side edges 122, 132 from the second end edges 128, 138 of the second and third webs 120, 130 to the second end edge 118 of the first web 110. Seal 154B is between the second web 120 and the third web 130 along respective second side edges 126, 136 from the second end edges 128, 138 of the second and third webs 120, 130 to the second end edge 118 of the first web 110. In an embodiment, the seals 154A, 154B may be peelable seals, weld seals, or other seals known to those skilled in the art and suitable for the purposes described herein. The second end edges 128, 138 of the second and third webs 120, 130 are not attached to each other, leaving an opening 142 for inserting the medical device MD into the cavity 140.

Still referring to FIG. 2, the portion of the pouch between the seal 152B and the first end edges 114, 134 of the first and third webs 110, 130 may be referred to as a cavity portion 170 of the pouch 100. Thus, the pouch 100 includes a header 160 (or header portion) and a cavity portion 160. As explained in more detail, below, the header portion 160 enables gas flow into the cavity 140 of the cavity portion 170 during sterilization, and then the cavity portion 170 may be sealed such that the cavity 140 of the pouch 100 becomes gas-impermeable.

Figure 4:
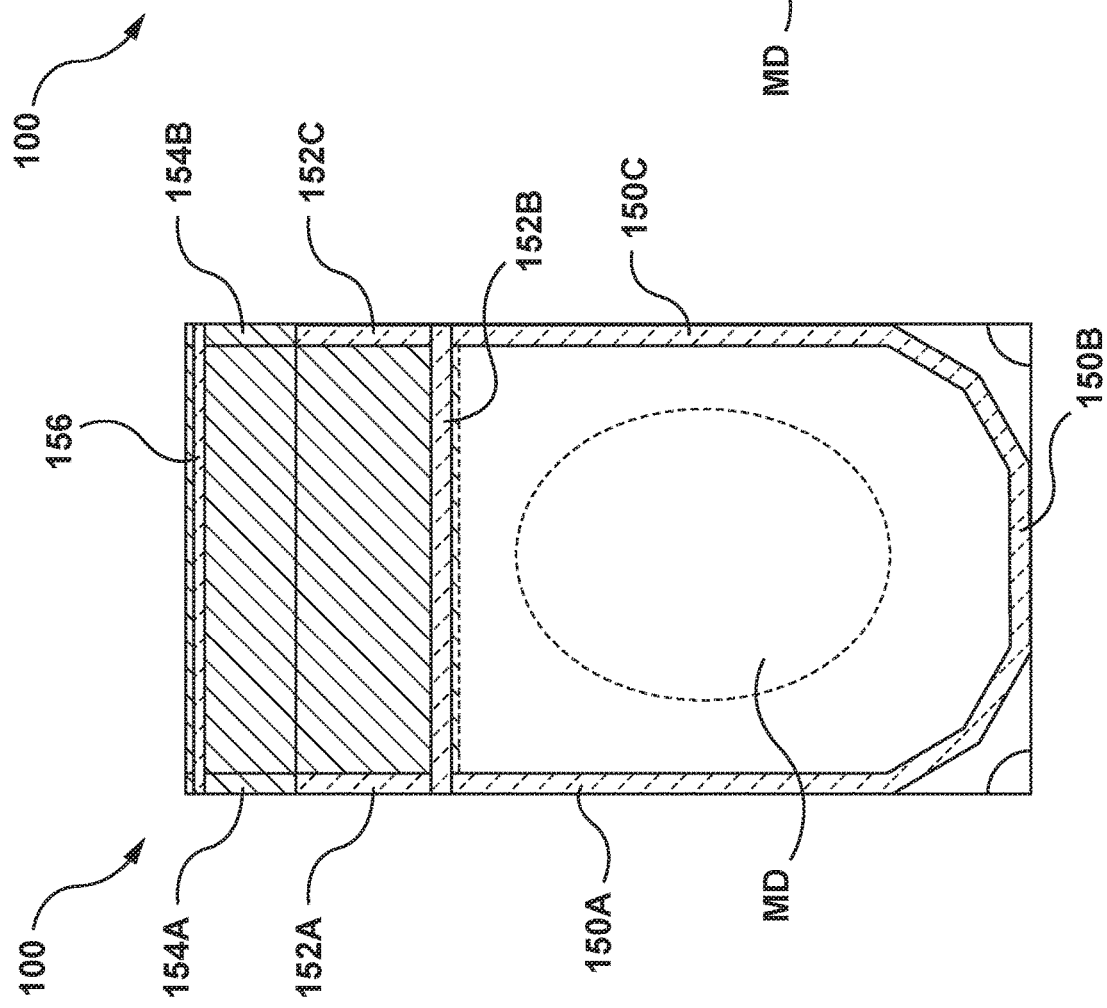
FIG. 4 is a schematic plan view of a step in a method of sterilization and sealing of a medical device within the pouch of FIG. 1 in accordance with an embodiment hereof.

With the construction of the pouch 100 described, a method for sterilizing and sealing the pouch 100 and the medical device MD disposed therein will now be described with reference to FIGS. 4-7. Starting with the pouch 100 as shown and described with respect to FIG. 2, the medical device MD is inserted through the opening 142 between the second web 120 and the third web 130 at respective second end edges 128, 138 of the second and third webs 120, 130, and into the cavity 140. The medical device MD is inserted into the cavity 140 such that the medical device is in the cavity portion 170 of the pouch 100, i.e., between the first end edge 124 of the second web 120 and the first end edges 114, 134 of the first and third webs 110, 130. In other words, the medical device MD is located in the portion of the pouch 100 with only the first and third webs 110, 130. With the medical device MD located in the cavity 140, a seal 156 seals the opening 142. In particular, the seal 156 seals the second web 120 to the third web 130 along respective second end edges 128, 138 thereof, as shown in FIG. 4. The seal 156 may be a weld seal, peelable seal, or other seal known to those skilled in the art and suitable for the purposes described herein.

With the medical device MD disposed within the cavity 140 and the opening 142 sealed by the seal 156, the pouch 100 with the medical device MD disposed therein is sterilized. In a particular example, ethylene oxide (EtO) sterilization is used. Due to the design of the pouch 100, the ethylene oxide can penetrate through the second web 120 as indicated by the arrows 162 shown in FIG. 3, and into the cavity 140.

Figure 5:
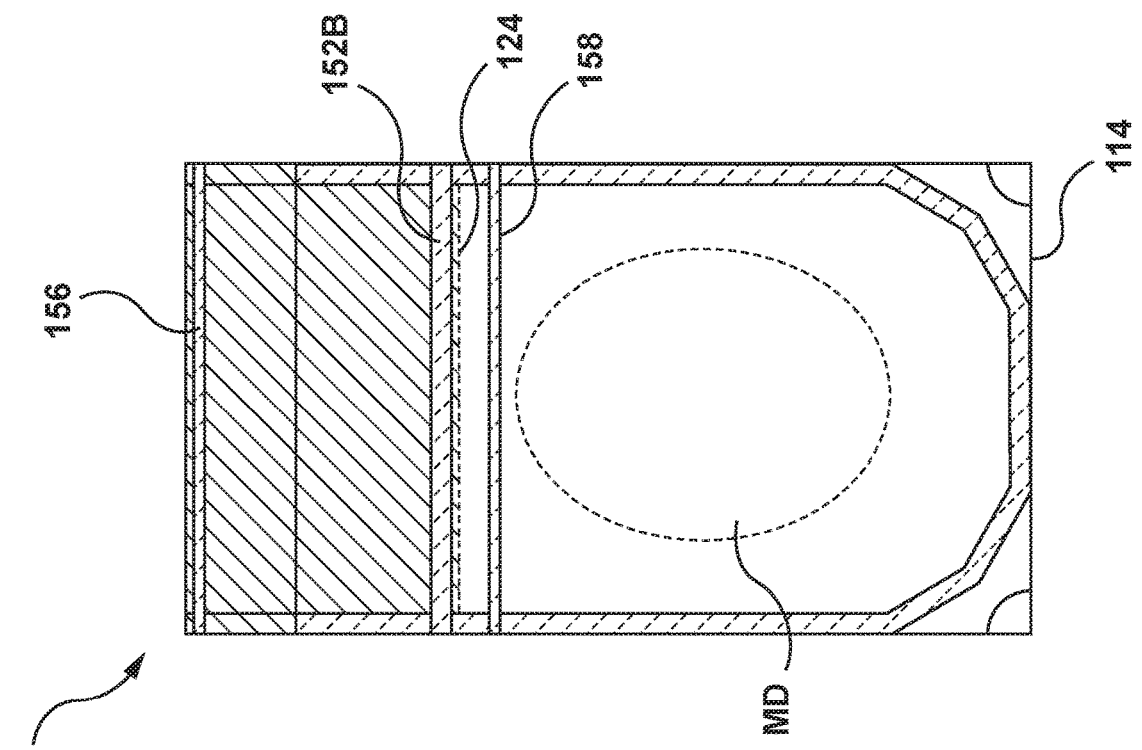
FIG. 5 is a schematic plan view of another step in the method of sterilization and sealing of a medical device within the pouch of FIG. 1 in accordance with an embodiment hereof.

When sterilization is complete, flushing and/or air extraction are performed. In a particular example, nitrogen gas flushing of the pouch and a vacuum cycle are performed to remove air from the cavity 140 of the pouch 100. A seal 158 is then formed between the first web 110 and the third web 130, as shown in FIG. 5. As explained above, due to the pocket 180, a flushing sealer with flushing arms may be used to flush and seal the pouch 100. Further, other types of flushing devices, such as available from MULTIVAC, may be used. The seal 158 extends generally parallel to the first and second end edges 114, 118, 134, 138 of the first web 110 and the third web 130. Further, the seal 158 is disposed between the first end edge 124 of the second web 120 and the first end edges 114, 134 of the first and third webs 110, 130, as shown in FIG. 5. As shown in FIG. 5, the seal 158 is adjacent the first end edge 124 of the second web 120 and the seal 152B to isolate the header 160 from the cavity portion 170. The seal 158 may be a weld seal, peelable seal, or other seal known to those skilled in the art and suitable for the purposes described herein.

With the pouch 100 sterilized, flushed, vacuumed, and sealed, the header 160 may be removed. In particular, the header 160 may be removed by cutting the along a line 159 substantially parallel to the first end edges 114, 134 of the first and third webs 110, 130 between the seal 158 and the header 160, as shown in FIG. 6. With the header 160 removed, the medical device MD is disposed within the cavity 140 of the cavity portion 170 and is surrounded by gas-impermeable first and third webs 110, 130. When the medical device MD is ready to be used, a user may grasp the first web 110 at one of the cut-outs 113, grasp the third web 130 adjacent the cut-out 113, and pull the first and third webs 110, 130 apart. Due to the peelable seals 150A, 150B, 150C, the first and third webs 110, 130 separate from each other at the peelable seals 150A, 150B, 150C, thereby exposing the medical device MD within the cavity 140.

Although specific features of the embodiment of FIGS. 1-7 have been described above, those skilled in the art would recognize that variations are possible without departing from the invention. For example, and not by way of limitation, sizes and shapes described with respect to FIGS. 1-7 may be varied provided that the principles of operation for the pouch 100 are maintained. Further, specific features such as cut-outs 113 may be eliminated or alternative means to achieve the results described may be used.

FIGS. 8-14 show a pouch 200 in accordance with another embodiment hereof. FIG. 8 shows an exploded view of the pouch 200. As can be seen in FIG. 8, the pouch 200 includes a first layer or web 210, a second layer or web 220, and a third layer or web 230, wherein the second web 220 is disposed at least partially between the first web 110 and the third web 230. In this specification, the first web 210 may also be referred to as a top layer or web, the second web 220 may be referred to as a middle layer or web, and third web 230 may be referred to as a bottom layer or web. However, it is recognized that labels regarding orientation, such as top and bottom, are not limiting in that the pouch 200 may be flipped such that the third web 230 is "on top". As used herein the term "layer" or "web" means a formed sheet that may be a laminate of several layers formed together. Thus, a laminate with several materials formed together as a single sheet is a single layer or web, not more than one layer, as would be understood by those skilled in the art. A cavity 240 for receiving a medical device MD is formed between the first web 110 and the third web 130, as best shown in FIG. 11A.

In the embodiment of FIGS. 8-14, the first web 210 is formed of a gas-impermeable film or foil material, such as, but not limited to aluminum, low-density polyethylene (LDPE), nylon, or polyester. The first web 210 provides an effective barrier against the migration of micro-organisms, including bacteria. In an example, and not by way of limitation, the first web 210 may be a material known as Polyester Foil Laminate RFR-085 available from Amcor. Similarly, the third web 230 is formed of a gas-impermeable film or foil material, such as, but not limited to aluminum, low-density polyethylene (LDPE), nylon, or polyester. The third web 230 may be formed of the same material and the first web 210, but it may be a different gas-impermeable web. For example, and not by way of limitation, in an embodiment, the third web 230 may be a material known as Plyester/Foil Core Peel LCP-545 available from Amcor. In the embodiment of FIGS. 8-14, the second web 220 is a gas-permeable material that is a barrier to microorganisms, but is permeable to gases including oxygen, carbon dioxide, and various sterilization gases such as, but not limited to ethylene oxide gas (EtO), steam sterilization methods, and other suitable sterilization methods. Suitable materials for the second web 220 may include medical grade paper and nonwoven sheet materials. Suitable nonwoven sheet material include spunbond nonwoven fabrics such as Typar® and Reemay® fabrics from Fiberweb Inc. Suitable materials also spun-bonded polyolefin marketed by DuPont under the name Tyvek®. In an example, and not by way of limitation, the second web 220 may be a material known as 1059B Uncoated Tyvek available from DuPont. The example materials provided above are not limiting. However, in the embodiment of FIGS. 8-14, the first and third webs 210, 230 are gas-impermeable, and the second web 220 is gas-permeable, as those terms are understood by those skilled in the art.

The first web 210 includes first and second side edges 212, 216, first and second end edges 214, 218, an outer surface 211, and an inner surface 215. The first web 210 also includes an opening or hole 219 extending from the outer surface 211 through the inner surface 215 of the first web 210. In the embodiment shown, the hole 219 is circular, but that is not limiting. The hole 219 may be any shape, such as, but not limited to, oval, rectangular, square, trapezoidal, etc. The hole 219 is sized to permit sufficient gas for sterilization to flow therethrough, as described in more detail below. In the embodiment shown, the hole 219 is offset towards the second end edge 218 of the first web 210, for reasons that will be clear when describing the sterilization and sealing method below. The first web 210 may also include cut-outs 213 where the first and second side edges 212, 216 meet the first end edge 214, as shown in FIGS. 8 and 9, for easy of peeling the first web 210 from the third web 230, as described in more detail below.

The second web 220 in the present embodiment is a patch that is configured to cover the hole 219 in the first web 210. Thus, the second web 220 is slightly larger than the hole 219 such that the second web 220 may be sealed to the first web 210, as described in more detail below. In the embodiment shown, the second web 220 is the same shape as the hole 219, but it need not be so provided that the second web 220 entirely covers the hole 219. The second web 220 includes a first surface 221 and a second surface 225.

The third web 230 includes first and second side edges 232, 236, first and second end edges 234, 238, an inner surface 235, and an outer surface 231. Although cut-outs 213 are described with respect to the first web 210, cut-outs could instead be provided in the third web 230. The third web 230 is aligned with the first web 210 such that the first and second side edges 212, 216 of the first web are generally aligned with the first and second side edges 232, 236 of the third web 230, and the first and second end edges 214, 218 of the first web 210 are generally aligned with the first and second end edges 234, 238 of the third web. In the embodiment shown the third web 230 has the same shape and dimensions of the first web 210, and while this is preferred, it is not required. Further, the shape and dimensions shown are exemplary and may be varied depending on, among other factors, the medical device to be housing within the cavity 240 of the pouch 200.

Having described the webs 210, 220, 230, the seals connecting the webs to each other will now be described with reference to FIG. 9. In the embodiment shown, the first web 210 is coupled to the third web 230 at seals 250A, 250B, and 250C. The seals 250A, 250B, and 250C form a generally U-shape and extend generally along the first side edges 212, 232, the first end edges 214, 234, and the second side edges 216, 236 of the first and third webs 210, 230. As shown in FIG. 9, along the first and second side edges 212, 232, 216, 236, the seals 250A, 250C begin at the second end edges 218, 238 of the first and third webs 210, 230. The seals 250A, 250B, and 250C are preferably peelable seals, as known to those skilled in the art. Peelable seals 250A, 250B, 250C also ease the method of aseptic technique practiced when removing the medical device MD from the pouch 200. Peelable seals 250A, 250B, 250C enable easy removal of the medical device MD from the pouch 200 when the medical device MD is ready to be used. The second end edges 218, 238 of the first and third webs 210, 230 are not sealed to each other at this time, thereby leaving an opening 242 between the first and third webs 210, 230 (see FIG. 9A) for a medical device MD to be inserted through, as described in more detail below.

Still referring to FIGS. 9 and 9A, the inner surface 215 of the first web 210 is sealed to the first surface 221 of the second web 220 at seal 254. The seal 254 may be generally the shape of and slightly larger than the hole 219 in the first web 210. The seal 254 is between the first web 210 and the second web 220 only. In other words, the second web 220 is not sealed to the third web 230. The seal 254 may be a weld seal, as known to those skilled in the art, or other seals suitable for the purposes described herein.

Still referring to FIG. 9, the pouch 200 can be described as having a header portion 260 and a cavity portion 270. The header portion 260 of the pouch 200 is defined from a side of the seal 254 closest to the first end edges 214, 234 of the first and third webs 210, 230 to the second end edges 218, 238 of the first and third webs 210, 230. The cavity portion 270 of the pouch 200 is defined from the side of the seal 254 closest to the first end edges 214, 234 of the first and third webs 210, 230 to the first end edges 214, 234 of the first and third webs 210, 230, and includes the cavity 240.

With the construction of the pouch 200 described, a method for sterilizing and sealing the pouch 200 and the medical device MD disposed therein will now be described with reference to FIGS. 10-14. Starting with the pouch 200 as shown and described with respect to FIGS. 9 and 9A, the medical device MD is inserted through the opening 242 between the first web 210 and the third web 230 at respective second end edges 218, 238 of the first and third webs 210, 230, and into the cavity 240, as shown in FIG. 10. The medical device MD is inserted into the cavity 240 such that the medical device is longitudinally between the second web 220 and the first end edges 214, 234 of the first and third webs 210, 230. In other words, the medical device MD is located in the portion of the pouch 200 with only the first and third webs 210, 230, also referred to as the cavity portion 270. With the medical device MD located in the cavity 240, a seal 256 seals the opening 242, as shown in FIGS. 11 and 11A. In particular, the seal 256 seals the first web 210 to the third web 230 along respective second end edges 218, 238 thereof, as shown in FIGS. 11 and 11A. The seal 256 may be a weld seal, peelable seal, or other seal known to those skilled in the art and suitable for the purposes described herein.

With the medical device MD disposed within the cavity 240 and the opening 242 sealed by the seal 256, the pouch 200 with the medical device MD disposed therein is sterilized. In a particular example, ethylene oxide (EtO) sterilization is used. Due to the design of the pouch 200, the ethylene oxide can penetrate through the hole 219 and the second web 220 as indicated by the arrows 262 shown in FIG. 11A.

When sterilization is complete, flushing and/or air extraction are performed. In a particular example, nitrogen gas flushing of the pouch and a vacuum cycle are performed to remove air from the cavity 240 of the pouch 200. As with the sterilization gas entering the cavity 240 through the hole 219 and the second web 220, gas for the flushing and/or vacuum may enter/exit the cavity 240 through the second web 220 and the hole 219, as shown by the arrows in FIG. 12.

After air has been removed from the cavity 240, a seal 258 is formed between the first web 210 and the third web 230, as shown in FIG. 13. The seal 258 extends generally parallel to the first and second end edges 214, 218, 234, 238 of the first web 210 and the third web 230. Further, the seal 258 is located such that the hole 219 and the second web 220 are located to a first side of the seal 258 (towards the seal 256) and the cavity 240 with the medical device MD disposed therein are located to a second side of the seal 258 opposite the first side and towards the first end edges 214, 234 of the first and third webs 210, 230. Thus, the seal 258 ensures that cavity 240 is defined by gas-impermeable material, that is, the sealed first and third webs 210, 230. The seal 258 may be a weld seal weld seal, peelable seal, or other seal known to those skilled in the art and suitable for the purposes described herein. As described above, the portion of the pouch 200 on the first side of the seal 258 may be referred to as a header portion 260, and the portion of the pouch 200 on the second side of the seal 258 may be referred to as the cavity portion 270.

With the pouch 200 sterilized, flushed, vacuumed, and sealed, the header 260 may be removed. In particular, the header 260 may be removed by cutting the along a line 259 to the first side of the seal 258 and substantially parallel to the first end edges 214, 234 of the first and third webs 210, 230 between the seal 258 and the hole 219, as shown in FIG. 14. With the header 260 removed, the medical device MD is disposed within the cavity 240 and surrounded by gas-impermeable first and third webs 210, 230. When the medical device MD is ready to be used, a user may grasp the first web 220 at one of the cut-outs 213, grasp the third web 230 adjacent the cut-out 213, and pull the first and third webs 210, 230 apart. Due to the peelable seals 250A, 250B, 250C, the first and third webs 210, 230 separate from each other at the peelable seals 250A, 250B, 250C, thereby exposing the medical device MD within the cavity 240.

Although specific features of the embodiment of FIGS. 8-14 have been described above, those skilled in the art would recognize that variations are possible without departing from the invention. For example, and not by way of limitation, sizes and shapes described with respect to FIGS. 8-14 may be varied provided that the principles of operation for the pouch 200 are maintained. Further, specific features such as cut-outs 213 may be eliminated or alternative means to achieve the results described may be used.

A pouch 300 in accordance with an embodiment hereof is shown in FIGS. 15-21. FIG. 15 shows an exploded view of the pouch 300. The pouch 300 is similar to the pouch 100 except that the pouch 300 does not include the pocket 180 of pouch 100 due to a shorter overlap between the second, permeable web and the first, non-permeable web, as will be described in more detail below. As can be seen in FIG. 15, the pouch 300 includes a first layer or web 310, a second layer or web 320, and a third layer or web 330, wherein the second web 320 is disposed partially between the first web 310 and the third web 330. In this specification, the first web 310 may also be referred to as a top layer or web, the second web 320 may be referred to as a middle layer or web, and third web 330 may be referred to as a bottom layer or web. However, it is recognized that labels regarding orientation, such as top and bottom, are not limiting in that the pouch 300 may be flipped such that the third web 330 is "on top". As used herein the term "layer" or "web" means a formed sheet that may be a laminate of several layers formed together. Thus, a laminate with several materials formed together as a single sheet is a single layer or web, not more than one layer, as would be understood by those skilled in the art. A cavity 340 for receiving a medical device MD is formed between the first web 310 and the third web 330, as shown in FIG. 18A.

In the embodiment of FIGS. 15-21, the first web 310 is formed of a gas-impermeable film or foil material, such as, but not limited to aluminum, low-density polyethylene (LDPE), nylon, or polyester. The first web 310 provides an effective barrier against the migration of micro-organisms, including bacteria. In an example, and not by way of limitation, the first web 310 may be a material known as Polyester Foil Laminate RFR-085 available from Amcor. Similarly, the third web 330 is formed of a gas-impermeable film or foil material, such as, but not limited to aluminum, low-density polyethylene (LDPE), nylon, or polyester. The third web 330 may be formed of the same material and the first web 310, but it may be a different gas-impermeable material. For example, and not by way of limitation, in an embodiment, the third web 330 may be a material known as Plyester/Foil Core Peel LCP-545 available from Amcor. In the embodiment of FIGS. 15-21, the second web 320 is a gas-permeable material that is a barrier to microorganisms, but is permeable to gases including oxygen, carbon dioxide, and various sterilization gases such as, but not limited to ethylene oxide gas (EtO), steam sterilization methods, and other suitable sterilization methods. Suitable materials for the second web 320 may include medical grade paper and nonwoven sheet materials. Suitable nonwoven sheet materials include spun-bond nonwoven fabrics such as Typar® and Reemay® fabrics from Fiberweb Inc. Suitable materials also include spun-bonded polyolefin marketed by DuPont under the name Tyvek®. In an example, and not by way of limitation, the second web 320 may be a material known as 1059B Uncoated Tyvek available from DuPont. The example materials provided above are not limiting. However, in the embodiment of FIGS. 15-21, the first and third webs 310, 330 are gas-impermeable, and the second web 320 is gas-permeable, as those terms are understood by those skilled in the art.

The first web 310 includes first and second side edges 312, 316, first and second end edges 314, 318, an outer surface 311, and an inner surface 315. The first web 310 may also include cut-outs 313 where the first and second side edges 312, 316 meet the first end edge 314, as shown in FIGS. 15 and 16, for easy of peeling the first web 310 from the third web 330, as described in more detail below. Similarly, the second web 320 includes first and second side edges 322, 326, first and second end edges 324, 328, a first surface 321, and a second surface 325. Similarly, the third web 330 includes first and second side edges 332, 336, first and second end edges 334, 338, an inner surface 335, and an outer surface 331. Although cut-outs 313 are described with respect to the first web 310, cut-outs could instead be provided in the third web 330. Referring to FIG. 16, the first web 310 has a first length L1, the second web 320 has a second length L2, and the third web 330 has a third length L3. The third length L3 of the third web 330 is greater than the first length L1 of the first web 310, which is greater than the second length L2 of the second web 330. Because the third web 330 is longer than the first web 310, with the first end edges 314, 334 of the first and third webs 310, 330 aligned, the second end edge 338 of the third web 330 extends past the second end edge 318 of the first web 310, as shown in FIGS. 15 and 16. As also shown in FIGS. 15 and 16, the length L2 of the second web 320 is such that with the second end edge 328 of the second web 320 aligned the second end edge 338 of the third web 330, the first end edge 324 of the second web 320 is disposed between the first and second end edges 314, 318 of the first web 310, thereby forming a header 360. In the embodiment of FIGS. 15-16, the amount of overlap OL between the first web 310 and the second web 320 is minimal such that the first end edge 324 of the second web 320 is near the second end edge 318 of the first web 310.

Having described how the webs 310, 320, 330 are oriented relative to each other, the seals connecting the webs to each other will now be described with reference to FIG. 16. In the embodiment shown, the first web 310 is coupled to the third web 330 at seals 350A, 350B, and 350C. The seals 350A, 350B, and 350C form a generally U-shape and extend generally along first side edges 312, 332, first end edges 314, 334, and second side edges 316, 336 of the first and third webs 310, 330. As shown in FIG. 16, along the first and second side edges 312, 332, 316, 336, the seals 350A, 350C begin where the overlapping of the first web 310 and the second web 320 ends. The seals 350A, 350B, and 350C are preferably peelable seals (also known as "peel seals"), as known to those skilled in the art. Peelable seals 350A, 350B, 350C enable easy removal of the medical device MD from the pouch 300 when the medical device MD is ready to be used. Peelable seals 350A, 350B, 350C also ease the method of aseptic technique practiced when removing the medical device MD from the pouch 300.

Still referring to FIG. 16, the first web 310 is sealed the second web 320 at seals 352A, 352B, and 352C. The seal 352A is between the first web 310 and the second web 320 along respective first side edges 312, 322 where the first and second webs 310, 320 overlap. Similarly, the seal 352C is between the first web 310 and the second web 320 along respective second side edges 316, 326 where the first and second webs 310, 320 overlap. The seal 352B is between the first web 310 and the second web 320, extends generally parallel to the first end edge 322 of the second web 320, and extends from the seal 352A to the seal 352C. At the location of seals 352A, 352B, and 352C, the third web 330 is located adjacent the second web 320 (i.e., below the second web 320 in FIG. 16), but the third web 330 is not sealed to the second web 320 or the first web 310 at the locations of the seals 352A, 352B, and 352C. In an embodiment, the seals 352A, 352B, and 352C are weld seals, as that term is understood by those skilled in the art.

Still referring to FIG. 16, the second web 320 is coupled to the third web 330 at seals 354A and 354B. Seal 354A is between the second web 320 and the third web 330 along respective first side edges 322, 332 from the second end edges 328, 338 of the second and third webs 320, 330 to the second end edge 318 of the first web 310. Seal 354B is between the second web 320 and the third web 330 along respective second side edges 326, 336 from the second end edges 328, 338 of the second and third webs 320, 330 to the second end edge 318 of the first web 310. In an embodiment, the seals 354A, 354B may be peelable seals, weld seals, or other seals known to those skilled in the art and suitable for the purposes described herein. The second end edges 328, 338 of the second and third webs 320, 330 are not attached to each other, leaving an opening 342 for inserting the medical device MD into the cavity 340.

Still referring to FIG. 16, the portion of the pouch between the seal 352B and the first end edges 314, 334 of the first and third webs 310, 330 may be referred to as a cavity portion 370 of the pouch 300. Thus, the pouch 300 includes a header 360 (or header portion) and a cavity portion 370. As explained in more detail, below, the header portion 360 enables gas flow into the cavity 340 of the cavity portion 370 during sterilization, and then the cavity portion 370 may be sealed such that the cavity 340 of the pouch 300 becomes gas-impermeable.

Figure 18A:
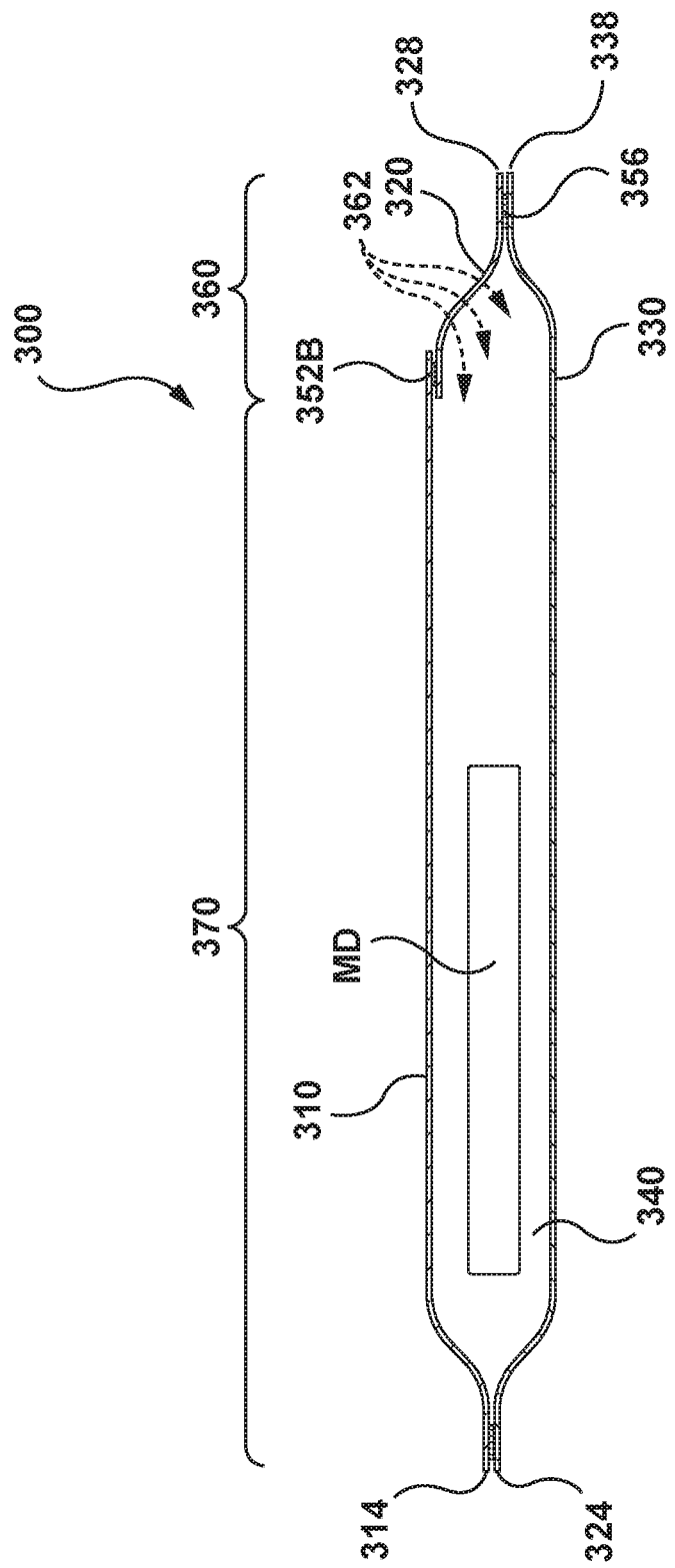
FIG. 18A is a schematic sectional view taken along line 18A-18A of FIG. 18.

With the construction of the pouch 300 described, a method for sterilizing and sealing the pouch 300 and the medical device MD disposed therein will now be described with reference to FIGS. 17-21. Starting with the pouch 300 as shown and described with respect to FIG. 16, the medical device MD is inserted through the opening 342 between the second web 320 and the third web 330 at respective second end edges 328, 338 of the second and third webs 320, 330, and into the cavity 340. The medical device MD is inserted into the cavity 340 such that the medical device is in the cavity portion 370 of the pouch 300, i.e., between the first end edge 324 of the second web 320 and the first end edges 314, 334 of the first and third webs 310, 330. In other words, the medical device MD is located in the portion of the pouch 300 with only the first and third webs 310, 330. With the medical device MD located in the cavity 340, a seal 356 seals the opening 342. In particular, the seal 356 seals the second web 320 to the third web 330 along respective second end edges 328, 338 thereof, as shown in FIG. 18. The seal 356 may be a weld seal, peelable seal, or other seal known to those skilled in the art and suitable for the purposes described herein. FIG. 18A shows a sectional view taken along line 18A-18A of FIG. 18 with the medical device MD disposed within the cavity 340 and the seal 356 sealing the opening 342.

With the medical device MD disposed within the cavity 340 and the opening 342 sealed by the seal 356, the pouch 300 with the medical device MD disposed therein is sterilized. In a particular example, ethylene oxide (EtO) sterilization is used. Due to the design of the pouch 300, the ethylene oxide can penetrate through the second web 320 as indicated by the arrows 362 shown in FIG. 18A, and into the cavity 340.

When sterilization is complete, flushing and/or air extraction are performed. In a particular example, nitrogen gas flushing of the pouch and a vacuum cycle are performed to remove air from the cavity 340 of the pouch 300, as shown in FIG. 19. A seal 358 is then formed between the first web 310 and the third web 330, as shown in FIG. 20. The seal 358 extends generally parallel to the first and second end edges 314, 318, 334, 338 of the first web 310 and the third web 330. Further, the seal 358 is disposed between the first end edge 324 of the second web 320 and the first end edges 314, 334 of the first and third webs 310, 330, as shown in FIG. 5. As shown in FIG. 20, the seal 358 is adjacent the first end edge 324 of the second web 320 and the seal 352B to isolate the header 360 from the cavity portion 370. The seal 358 may be a weld seal, peelable seal, or other seal known to those skilled in the art and suitable for the purposes described herein.

With the pouch 300 sterilized, flushed, vacuumed, and sealed, the header 360 may be removed. In particular, the header 360 may be removed by cutting the along a line 359 substantially parallel to the first end edges 314, 334 of the first and third webs 310, 330 between the seal 358 and the header 360, as shown in FIG. 21. With the header 360 removed, the medical device MD is disposed within the cavity 340 of the cavity portion 370 and is surrounded by gas-impermeable first and third webs 310, 330. When the medical device MD is ready to be used, a user may grasp the first web 310 and the third web 330 at one of the cut-outs 313 and pull the first and third webs 310, 330 apart. Due to the peelable seals 350A, 350B, 350C, the first and third webs 310, 330 separate from each other at the peelable seals 350A, 350B, 350C, thereby exposing the medical device MD within the cavity 340.

Although specific features of the embodiment of FIGS. 15-21 have been described above, those skilled in the art would recognize that variations are possible without departing from the invention. For example, and not by way of limitation, sizes and shapes described with respect to FIGS. 15-21 may be varied provided that the principles of operation for the pouch 300 are maintained. Further, specific features such as cut-outs 313 may be eliminated or alternative means to achieve the results described may be used.

In some instances, the formation of the various seals has been described specifically as separate processes, but this is by way of example and not limitation, and it may be advantageous to form multiple seals simultaneously.

While the pouches described herein are shown with a generally rectilinear shape, this is by way of example and not limitation, and it will be understood that embodiments of pouches of the present disclosure may assume other shapes, such as oval, round, or virtually any desired shape.

Although described herein with specific examples of materials for the layers of the pouch embodiments, the specific materials of each layer of each embodiment may be selected based on the desired durability requirements of the pouch, permeability, and the sterilization method used.

While various embodiments according to the present invention have been described above, it should be understood that they have been presented by way of illustration and example only, and not limitation. Various changes in form and detail can be made therein without departing from the spirit and scope of the invention. Further, each feature of each of the embodiments described may be combined and/or interchanged with the features of any of the other embodiments described herein. Thus, the breadth and scope of the present invention should not be limited by any of the above-described exemplary embodiments, but should be defined only in accordance with the appended claims and their equivalents.

What is claimed is:

1. A flexible, sterilizable pouch comprising:
a first web, the first web being gas-impermeable and having a first length;
a second web, the second web being gas-permeable and having a second length;
a third web, the third web being gas-impermeable and having a third length, wherein the third length is longer than the first and second lengths such that with first end edges of the first and third webs aligned, a second end edge of the third web extends past a second end edge of the first web;
a cavity formed between the first web and the third web;
a header defined from a first end edge of the second web overlapping with the second end edge of the first web and sealed to an inner surface of the first web to a second end edge of the second web aligned with the second end edge of the third web with the second web sealed to an inner surface of the third web; and
a pocket formed between the first end edge of the second web and the second end edge of the first web, wherein the pocket is configured to receive flushing arms of a flushing sealer.

2. The pouch of claim 1, further comprising an opening formed between the second end edge of the second web and the second end edge of the third web due to the respective second end edges of the second and third webs not being sealed to each other.

3. The pouch of claim 2, wherein the opening is configured to be sealed after a medical device is inserted therethrough and into the cavity, thereby forming a sealed pouch that is gas-permeable through the header.

4. The pouch of claim 3, wherein the cavity of the pouch is configured to be made gas-impermeable by a seal between the first web and the third web formed after a sterilization process, wherein the seal is generally parallel to the first and second end edges of the first and third webs, and wherein the seal is disposed longitudinally between the first end edge of the second web and the first end edges of the first and third webs.

5. The pouch of claim 4, wherein the header is configured to be removed after the seal between the first and third webs is formed.

6. The pouch of claim 5, wherein the cavity is defined by the inner surfaces of the first and third webs, seals between the first and third webs along corresponding first and second side edges of the first and third webs and along the first end edges of the first and third webs, and the seal formed after the sterilization process.

7. The pouch of claim 1, wherein first web and the second web overlap for approximately 3 inches between the second end edge of the first web and the first end edge of second web.

8. A method of sterilizing a medical device and sealing the medical device within a pouch, the method comprising:
inserting the medical device through an opening in the pouch, the pouch including a first gas-impermeable web, a second gas-permeable web, and a third gas-impermeable web, wherein the first and third gas-impermeable webs are sealed to each other along corresponding first and second side edges and first end edges of the first and third gas-impermeable webs, wherein a second end edge of the third gas-impermeable web extends past a second end edge of the first gas-impermeable web, wherein a first end edge of the second gas-permeable web is sealed to an inner surface of the first gas-impermeable web in an overlapping fashion such that the second end edge of the first gas-impermeable web extends past the first end edge of the second gas-permeable web to form a pocket configured to receive flushing arms of flushing sealer, wherein the second gas-permeable web is sealed to the third gas-impermeable web along corresponding first and second side edges of the second and third gas-impermeable webs, and wherein the opening is formed by corresponding second end edges of the second gas-permeable web and the third gas-impermeable web that are not attached to each other;
sealing the opening after inserting the medical device through the opening;
exposing the pouch to a sterilizing gas under conditions to sterilize the medical device, wherein the sterilizing gas reaches the medical through the second gas-permeable web; and
after sterilizing the medical device, removing air from the cavity and forming a final seal between the first and third gas-impermeable webs generally parallel to the first and second end edges of the first and third gas-impermeable webs, wherein the final seal is located longitudinally between the first end edge of the second gas-permeable web and the first end edges of the first and third gas-impermeable webs.

9. The method of claim 8, further comprising:
after forming the final seal, removing a portion of the pouch between the final seal and the second edge edges of the second gas-permeable web and the third gas-impermeable web.

10. The method of claim 9, wherein removing the portion of the pouch comprises cutting the pouch along a line between the final seal and the first end edge of the second gas-permeable web.

11. A flexible, sterilizable pouch comprising:
a first web, the first web being gas-impermeable and having a first length defined between a first web first end edge and a first web second end edge;
a second web, the second web being gas-permeable and having a second length defined between a second web first end edge and a second web second end edge;
a third web, the third web being gas-impermeable and having a third length defined between a third web first end edge and a third web second end edge, wherein the third length is longer than the first and second lengths such that with first web first end edge and the third web first end edge aligned, the third web second end edge extends past the first web second end edge;
a cavity formed between the first web and the third web;
a header defined from the second web first end edge overlapping with the first web second end edge and sealed to an inner surface of the first web to the second web second end edge aligned with the third web second end edge with the second web sealed to an inner surface of the third web; and
a pocket formed between the second web first end edge and the first web second end edge of the first web, wherein the first web second end edge is not sealed to the second web such that the pocket is configured to receive flushing arms of a flushing sealer between the first web and the second web.

12. The pouch of claim 11, further comprising an opening formed between the second web second end edge and the third web second end edge due to the second web second end edge and the third web second end edge not being sealed to each other.

13. The pouch of claim 12, wherein the opening is configured to be sealed after a medical device is inserted therethrough and into the cavity, thereby forming a sealed pouch that is gas-permeable through the header.

14. The pouch of claim 13, wherein the cavity of the pouch is configured to be made gas-impermeable by a seal between the first web and the third web formed after a sterilization process, wherein the seal is generally parallel to the first web first edge, the first web second edge, the third web first edge, and the third web second edge, and wherein the seal is disposed longitudinally between the second web first end edge and the first web first end edge.

15. The pouch of claim 14, wherein the header is configured to be removed after the seal between the first and third webs is formed.

16. The pouch of claim 15, wherein the cavity is defined by the inner surfaces of the first and third webs, seals between the first and third webs along corresponding first and second side edges of the first and third webs and along the first web first end edge and the third web first edge, and the seal formed after the sterilization process.

17. The pouch of claim 11, wherein the pocket is further defined by first and second side edges of the first web and the second web sealed together between the second web first edge and the first web second edge.

* * * * *